United States Patent
Zhang et al.

(10) Patent No.: US 7,227,040 B2
(45) Date of Patent: Jun. 5, 2007

(54) PROCESS FOR FORMING BRANCHED COMPOSITION CATALYTICALLY BY CARBON-HYDROGEN BOND ACTIVATION IN A SATURATED MOIETY

(75) Inventors: Zongchao Zhang, Norwood, NJ (US); Xiaolei Sun, Yonkers, NY (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/862,758

(22) Filed: Jun. 7, 2004

(65) Prior Publication Data

US 2005/0272941 A1    Dec. 8, 2005

(51) Int. Cl.
*C07C 209/68* (2006.01)

(52) U.S. Cl. ............ 564/463; 564/336; 564/470; 558/303; 549/83; 549/86; 546/184

(58) Field of Classification Search ............ None
See application file for complete search history.

(56) References Cited

U.S. PATENT DOCUMENTS

| | | | | |
|---|---|---|---|---|
| 4,165,439 A | 8/1979 | Smith | ............ | 568/804 |
| 5,925,793 A | 7/1999 | Mueller | ............ | 564/480 |
| 6,127,309 A | 10/2000 | Aida et al. | ............ | 502/217 |
| 6,451,937 B1 | 9/2002 | Hartwig et al. | ............ | 526/126 |
| 6,469,225 B1 | 10/2002 | Basset et al. | ............ | 585/708 |
| 2001/0039349 A1 | 11/2001 | Hartwig et al. | ............ | 546/250 |

FOREIGN PATENT DOCUMENTS

| | | |
|---|---|---|
| EP | 1259517 | 11/2002 |
| GB | 534539 A | 3/1941 |
| WO | 00/27781 | 5/2000 |
| WO | 03/066552 | 8/2003 |

OTHER PUBLICATIONS

Database CAPLUS on STN, Acc. No. 1910:8232, Freylon, Annales de Chimie et de Physique (1910), 19, p. 551-574 (abstract).*
Database CAPLUS on STN, Acc. No. 1911:19248, Mailhe et al., Bull. soc. chim. (1911), p. 464-468 (abstract).*

* cited by examiner

*Primary Examiner*—Brian Davis
(74) *Attorney, Agent, or Firm*—Ralph J. Mancini; Richard p. Fenn

(57) ABSTRACT

A branched composition can be formed by reacting a reagent containing a saturated hydrocarbon moiety in the presence of (a) a catalyst capable of activating a carbon-hydrogen bond therein and (b) a branching reagent having a moiety that binds to the carbon atom in the carbon-hydrogen bond upon extraction of the hydrogen atom from that carbon-hydrogen bond. Suitable catalysts are those that comprise a transition metal cation possessing multiple oxidation states that is embedded in an anion that is a transition metal oxide possessing a higher oxidation state for the metal therein than the metal in the cation.

9 Claims, No Drawings

PROCESS FOR FORMING BRANCHED COMPOSITION CATALYTICALLY BY CARBON-HYDROGEN BOND ACTIVATION IN A SATURATED MOIETY

One of the key challenges in chemistry has been the activation of C—H bonds and formation of C—C bonds in saturated hydrocarbons. There are a few known organic chemistries for C—C bond formation and all involve multiple synthesis steps and are only applicable to activated bonds. Examples of these reactions follow.

The Mirozoki-Heck and Suzuki Reactions:

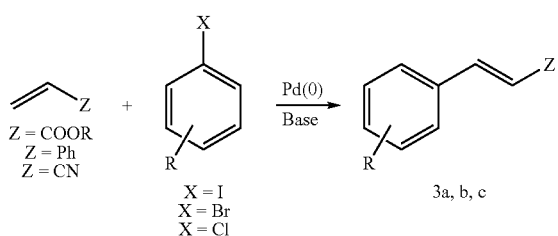

Suzuki Cross Coupling:

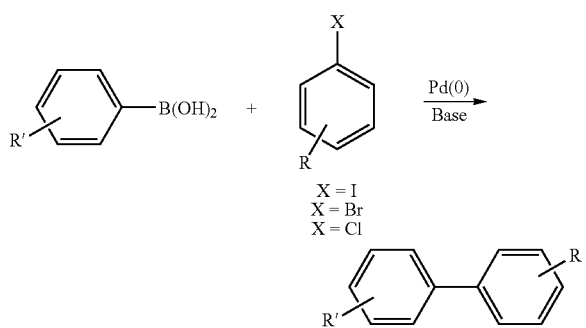

Stille Cross Coupling:

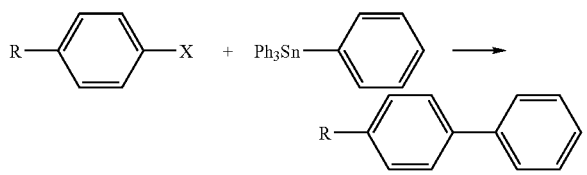

Polymerization involves C—C forming chemistry, but it only applies to unsaturated hydrocarbons, and does not involve C—H activation. Alkylation also forms C—C bond, but it only works for aromatic substrates and an olefin or an alkyl halide.

For many years, chemists around the globe have been actively pursuing the ability to activate the C—H bond in saturated hydrocarbon structures. It is a challenge that has been widely recognized with limited success that is far from being commercially practical.

Dendrimer molecules can be constructed with a controlled architecture. Given a structural motif, dendrimers radiate from a central core and comprise branches-upon-branches to form well-defined macromolecules. Dendrimers have some proven applications and numerous potential applications. They have been used in the production of industrial adhesives and are expected to serve as components in a variety of nanomachines. Dendrimers are of interest to researchers in medical technology, where they might help carry and deliver drugs in the body or serve as replacements for plasma components. Dendrimers might also prove useful in the manufacture of nanoscale batteries and lubricants, catalysts, and herbicides.

However, the synthesis of dendrimers has been a repetitive task involving multiple generations of building successive shells. The three main synthetic approaches, namely, the starburst divergent strategy, the convergent strategy, and the self-assembly strategy, have generated dendrimers with a variety of properties and applications, which range from the preparation of new drug delivery systems to inks. An important potential application of dendrimers is the encapsulation of molecules.

Branched fatty acids have been made by isomerization of unsaturated linear fatty acids using zeolite catalysts. Saturated branched fatty acids are attractive in many applications as they have lower melting points and are more stable than unsaturated molecules. Even though fatty amine-derived products are also expected to have superior properties by skeletal isomerization, there is no direct route to synthesize the branched fatty amines from linear ones. The production of saturated fatty amines from unsaturated fatty acids incurs a high raw material and processing cost. Saturated fatty amines can be produced from saturated fatty acids, but the challenge remains in the isomerization of saturated fatty acids to branched ones.

The present invention comprises a novel chemistry that allows for the direct synthesis of branched molecules, including amines. The present approach is unprecedented and represents an important breakthrough that allows for the more direct synthesis of a wide range of new products that have not been possible based on existing synthetic approaches.

One embodiment of the invention involves the additive branching of saturated linear fatty amines by the reaction of a linear fatty amine with an alcohol or a lower amine in the presence of a suitable catalyst. Some C—H bonds in the fatty amine are activated and at the same time a branch, derived from the alcohol, lower amine, or alkylamine itself is additively formed on the carbon with $NH_3$ and/or $H_2O$ as by-products. For example, the alkyl group of the alcohol can be linked to the fatty chain as a branch using this method. The fatty amine can be nearly fully converted using this reaction scheme:

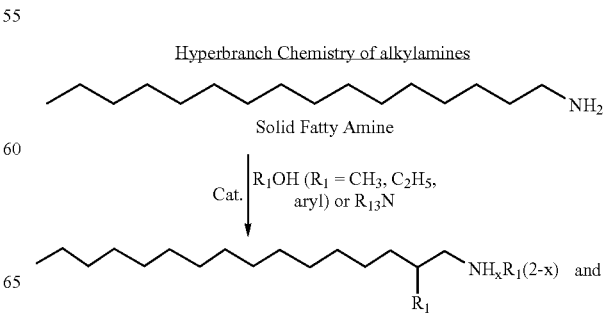

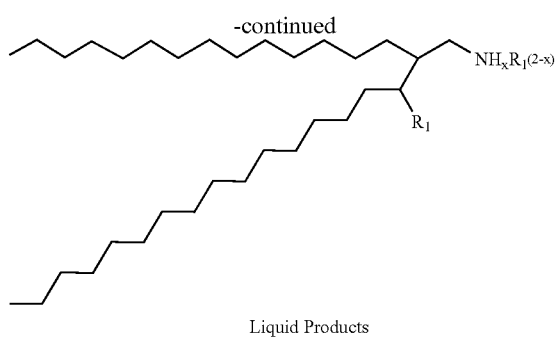

Liquid Products

As particular examples of this chemical approach, the reaction of hexadecylamine (a solid feed) with methanol and ethanol resulted in the formation of clear liquid products with methyl, ethyl, and hexyl branches, respectively. MALDI and NMR analysis of the products confirmed the formation of hyper-branched products. More than 80% of the branches are on the β-carbon position, with the rest of them being at higher positions.

A further demonstration of the present invention was the formation of higher branched amine products by employing a short chain alkylamine and an alcohol. In this embodiment, hexylamine and ethanol were used as the feed reagents.

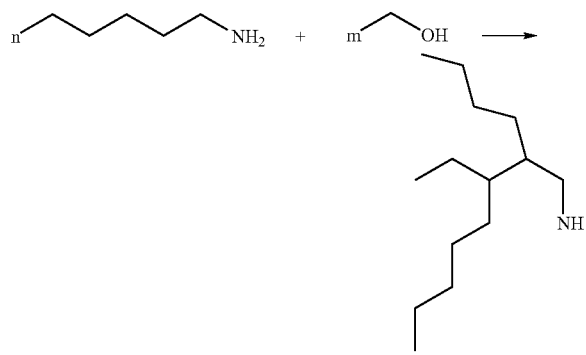

A very attractive feature of this new chemistry is that, for the first time, it enables the activation of C—H bond(s) in a saturated hydrocarbon chain and at the same time the formation of new C—C bond(s) to the saturated carbon after hydride cleavage.

The chemistry also allows the formation of dendritic polymers in a single simple process. Various functional groups may be incorporated through the synthesis. Using the reaction of fatty amine and alcohol as an example, the density and the size of the dendrimers could be controlled by varying the ratio of the alcohol to the amine.

The feed for the process of the present invention can be derived from a wide variety of commodity chemicals including alkylamines, alcohols, and hydrocarbons (saturated and unsaturated). By analogy, feedstocks may also include phosphorus and sulfur chemicals. Molecules with other heteroatoms may also be used. With a high alcohol to amine ratio, highly dense dendritic-type molecules can be synthesized in one single step.

Hyper-branched hydrocarbon products with low melting point and with a controllable molecular weight can be produced through the novel catalytic chemistry of the present invention. The molecular weight of the products will span that of dimers and trimers to that of moderate polymers.

The products can incorporate a wide variety of functional groups and branched structures. The functional groups can include amines, nitriles, amides, phosphates, sulfates, carboxylic acids, sulfonic acids, and other functionalities containing other heteroatoms. Unsaturated and aromatic features can also be introduced into the products to allow further processing to high performance materials with potential applications in many industries including pharmaceutical, coatings, and materials. With certain functional groups, the products can be applied in high performance resins with unprecedented properties.

This invention relates to novel chemistry for the synthesis of a broad range of branched products. It is based on a catalytic system that allows for C—H bond activation and C—C bond formation in saturated hydrocarbon chains. The chemistry can be used to synthesize a wide variety of hyper branched molecules from feedstocks that contain different functional groups. It has been demonstrated, for example, that this invention can effectively convert alkyl amines $(R^1NH_2)$ and lower alcohols $(R^2OH)$ or amines $[R^2_xNH_{(3-x)}]$ to branched heavier amines. The alkyl amines of different alkyl $(R^1)$ chain length are suitable starting reagents into which the alkyl groups $(R^2)$ from alcohols and other amines can be introduced. The process involves the cleavage of at least one C—H bond in the reagent alkyl amine $(R^1NH_2)$ and the formation of a C—C bond by the addition at least one alkyl group $(R^2)$ from an alcohol $(R^2OH)$ or from another alkyl amine $[R^2_xNH_{(3-x)}]$ source, or at least one alkyl group $(R^1)$ from the reagent alkyl amine $(R^1NH_2)$ to the same carbon(s) in $R^1$ after C—H cleavage to form both $R^1$ and $R^2$-containing branched alkyl amines. Reagent alkyl amines for use in the process can include the primary and secondary amines. This reagent may also contain other functional groups containing an N, S, P, or Si atom. The alcohols and other amines include aliphatic and aromatic alcohols and amines, optionally containing other functional groups, such as olefins and glycols.

The type of catalyst that is useful in regard to the present invention comprises a transition metal-containing cation possessing multiple oxidation states that is embedded in an anion that is a transition metal oxide possessing a higher oxidation state for the metal therein than the metal in the cation.

The transition metal or metals in the cation portion of such a catalyst can be selected from Group VIIB to IIB of the Periodic Table in the first (Mn, Fe, Co, Ni, Cu, and Zn), second (Tc, Ru, Rh, Pd, Ag, and Cd) and third (Re, Os, Ir, Pt, Au, and Hg) rows thereof. Either a single transition metal can be employed in the cation portion of the catalyst or more than one transition metal can be utilized.

The metal in the anion portion of such a catalyst can be selected from Group IIIB to VIB of the Periodic Table in the first (Sc, Ti, V, and Cr), second (Y, Zr, Nb, and Mo) and third (La, Hf, Ta, and W) rows thereof.

Modifiers that can also be present in the catalyst composition (at from about 0.1% to about 20%, more typically from about 0.5% to about 10%, by weight of the catalyst) include the alkali metals (such as K) and/or the alkaline earth metals (such as Ba) and/or the post transition metal elements from Groups IIA to VIA of the Periodic Table of the Elements.

Some typical catalysts that can be employed include those based on copper chromite, copper molybdate, copper chromate, copper tungstate, and copper vanadate.

Appropriate catalyst loadings for a batch reaction are from about 0.01% to about 20%, more typically from about 0.1% to about 5%, by weight of the reactants. In a continuous flow reaction, the catalyst loading can be from about 0.001 to about 1000 $hr^{-1}$, more typically from about 0.1 to about 10 $hr^{-1}$.

The hydrocarbon substrate (or mixture of such substrates) in the feed can comprise one or more heteroatoms. Representative heteroatoms include nitrogen (e.g., the amine, pyrrole, imidazole, pyridine, and/or nitrile reagent choices), sulfur (e.g., the thiophene, thiol, and/or sulfide reagent choices), phosphorus (e.g., the phosphine and/or phosphite reagent choices), boron (e.g., a borane reagent), oxygen (e.g., the alcohol, ether, carboxylic acid, and/or furan reagent choices), and halogen (e.g., a halogenated hydrocarbon reagent).

The branching reagent can be selected from the preceding list of heteroatom possibilities just described above for the substrate thereby giving a very wide variety of possibilities for this novel chemical approach.

In the case of amine and thiol substrates, it has been found that the branching predominantly occurs at the beta position to the amine or thiol group. With both nitrile and thiophene reagents the branching is mainly at the alpha position to the nitrile and thiol functionality, respectively. Aromatic compounds, both with and without heteroatoms in their ring have branching that takes the form of alkylation on the ring.

The present invention is further illustrated by the Examples that follow.

EXAMPLES 1 to 1B

Hexadecylamine with Alcohols

Methanol and hexadecylamine were introduced into a 300 ml autoclave reactor at a molar ratio of 4:1, and a 1 wt % copper chromite-containing catalyst ($Ba/CuCr_2O_4$) was charged to the reactor. The loaded reactor was then purged with nitrogen for about fifteen minutes. The reactor then was heated to 350° C. and was maintained at this temperature for twenty-four hours. After separating the solid catalyst by centrifuge, followed by filtration, two immiscible liquid products were obtained: an organic liquid product (top layer); and an aqueous product (bottom layer).

The organic product was analyzed by GC, NMR, FTIR and MALDI. MALDI chromatogram showed that there were five groups of multi-branched alkyl amine product clusters, each separated by a multiple of 224 Da, (associated with the mass of a hexadecyl group). These five groups were identified as being monoalkyl, dialkyl, trialkyl, tetraalkyl, and multialkyl. With the exception of the first group, each group had at least four products separated by 14 Da (associated with a $CH_3$ branch). Branching due to the presence of a hexadecyl group was also identified, $R'_{16}N(CH_3)_2/(R'_{16})_2NCH_3/N(R'_{16})_3$, at relative ratios of 1.00/1.07/0.22, where $R'_{16}$ represents multiple branched methyl and hexadecyl groups over a hexadecyl group. The hexadecylamine feed conversion was near 100%.

By following the same procedure, the reaction of hexadecylamine and ethanol was carried out for six hours at 350° C. using the same $Ba/CuCr_2O_4$ catalyst. An organic liquid product was obtained. GC analysis of the liquid product showed a very similar pattern as that obtained from the previously described reaction of hexadecylamine with methanol. Ethyl and hexadecyl branches were formed. The hexadecylamine conversion was about 90%.

EXAMPLE 2

Hexadecylamine with Trialkylamine

The reaction of hexadecylamine with triethylamine was conducted according to the procedure described in the previous Examples. Triethylamine and hexadecylamine were introduced into a 300 ml autoclave reactor at a molar ratio of 4:1. A 1 wt % copper chromite-containing catalyst ($Ba/CuCr_2O_4$) was then charged to the reactor, and the reaction was carried out at 350° C. for twenty-four hours. After separating the solid catalysts by centrifuge, a partial liquid/partial waxy solid product was obtained. The GC analysis of the liquid product showed a similar pattern to the one using ethanol in the feed, which indicated the formation of a product containing ethyl and hexadecyl branches. The hexadecylamine conversion was about 100%.

EXAMPLE 3

Hexadecylamine with Phenol

Following the same experimental procedure as descried in Examples 1 to 1B, phenol, in the form of white crystals, was mixed with solid hexadecylamine before the reactor was purged with nitrogen. The feed ratio of hexadecylamine to phenol was 1:4, and a 1 wt % copper chromite-containing catalyst ($Ba/CuCr_2O_4$) was used. The reaction was carried out at 350° C. for seven hours. A darkly colored liquid product was formed. GC analysis showed that the final product contained phenyl and hexadecyl branched products.

EXAMPLE 4

Hexadecylamine with Glycol

Following the same experimental procedure as descried in Examples 1 to 1B, the reaction of hexadecylamine with ethylene glycol at a feed ratio (1:4) and with the same catalyst loading yielded dark liquid products. The reaction lasted fifteen hours at 325° C. N-hexadecyl pyrrole and branched products were formed. The hexadecylamine conversion was about 100%.

EXAMPLE 5

Hexadecylamine with Olefin

Following the same experimental procedure as described in Examples 1 to 1B, the reaction of hexadecylamine with hexene (1:4) also yielded liquid products. The same catalyst was used. The synthesis process was carried out at 325° C. for fourteen hours. The GC/MS analysis showed that hexadecylnitrile ($C_{15}H_{31}CN$) and hexyl-branched hexadecylnitriles ($C_{21}H_{31}CN$) were formed. The hexadecylamine conversion was about 100%.

EXAMPLE 6

Hexylamine with Alcohol

The reaction of hexylamine with methanol was conducted according to the procedure as described in Examples 1 to 1B. Methanol and hexylamine were introduced into a 500 ml autoclave reactor at a molar ratio of 4:1. A 1 wt % copper chromite-containing catalyst ($Ba/CuCr_2O_4$) was used. The reaction was carried out at 350° C. for twenty-eight hours.

MALDI analysis for the final liquid product showed that the hyper-branched amine products, with ethyl and hexyl branches, were formed. The conversion of hexylamine was about 92%.

EXAMPLE 7

Octylamine

Following experimental procedure and with the same catalyst as described in Example 1 to 1B, octylamine was charged into the reactor as the only starting material. The synthesis procedure was carried out at 325° C. for six hours. The GC/MS analysis showed that branched dioctylamine, branched trioctylamine and multioctylamine were formed. The octylamine conversion was about 85%.

The following schematic shows the formation of a branched alkylamine product by the direct alkylation of fatty (or saturated) amines ($R^2NH_2$) with short chain alkyl alcohols ($R^1OH$) or amines ($R^1{}_3N$). The same mechanism can be applied to the other primary amines, such as octylamine and hexylamine, as demonstrated above.

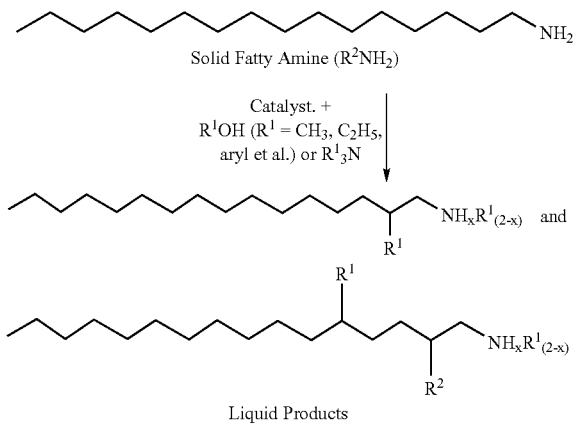

EXAMPLES 8 TO 8D

Alkylnitrile with Trialkylamine

The reaction of octanenitrile with triethylamine was conducted in a 30 ml autoclave reactor. Triethylamine and hexadecylamine were introduced at a molar ratio of 5:1. A 1 wt % copper chromite catalyst ($CuCr_2O_4$) was charged to the reactor. The reactor was purged with nitrogen before the temperature was increased, and the reaction was carried out at 350° C. for six hours. The product, after removal from the reactor, was then centrifuged to separate the catalyst. Octanenitrile gave a 44% conversion. Based on the GC/MS CI analysis, a product having an Mw of 153 Da had been formed. Since octanenitrile has an Mw of 125 Da, and one ethyl branch represents an additional molecular weight of 28 Da, the octanenitrile was determined to be branched with an ethyl group.

Utilizing the same operating conditions, 5% $K/CuCr_2O_4$, 5% $Zn/CuCr_2O_4$, 5% $Mn/CuCr_2O_4$ were also tested, and they all gave a similar product distribution by GC analysis.

EXAMPLE 9

Thiophene with Alcohol

Following the same experimental procedure as described in Examples 8 to 8D and with the same catalyst loading (1 wt %), the reaction of 3-octyl thiophene with methanol (1:5) was carried out using a 2% $Co/CuCr_2O_4$ catalyst. The reaction was conducted at 350° C. for six hours. By GC/MS CI analysis, the product was determined to have an Mw of 210 Da. The Mw of 3-octyl thiophene is 196 Da, and one methyl branch would produce an additional molecular weight of 14 Da. Combined with NMR analysis, 3-octyl thiophene was determined to be branched with a methyl group by employing this synthesis procedure. The conversion was about 10% to 3-octyl thiophene.

EXAMPLE 10

Thiophene with Olefin

Following the same experimental procedure as described in Examples 8 to 8D and with the same catalyst loading (1 wt %), the reaction of 3-octyl thiophene and hexene (1:5) was conducted at 350° C. for six hours. A 2% $Co/CuCr_2O_4$ catalyst was used. The reaction gave a product having an Mw of 280 Da based on GC/MS CI analysis. Since octanenitrile has an Mw of 196 Da and one hexyl branch represents an additional molecular weight of 84 Da, the 3-octyl thiophene was branched with a hexyl group by this process. The conversion was about 14% to 3-octyl thiophene.

EXAMPLE 11

Saturated Hydrocarbons with Mixed-Alkylamine

The reaction of hexadecane with triethylamine was conducted with the presence of piperidine. The feed ratio of hexadecane:piperidine:triethylamine was 1:1:8. A 1 wt % $Ba/CuCr_2O_4$ catalyst was used. The reaction temperature was 325° C., the reaction time was six hours, and a 300 ml autoclave reactor was used. The loaded reactor was then purged with nitrogen for about fifteen minutes. A liquid product was obtained after separating solid catalyst by centrifuge. Based on the GC/MS analysis, alkylated piperidine (with branched and/or unbranched structures) and alkylated trialkylamine (with branched and/or unbranched structures) were formed as products. The schematic given below shows the type of structures for the products that were obtained. The catalyst showed the capability to activate the saturated hydrocarbon. The hexadecane conversion was about 15%.

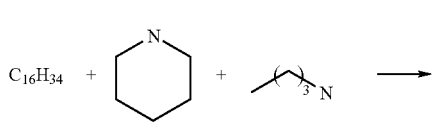

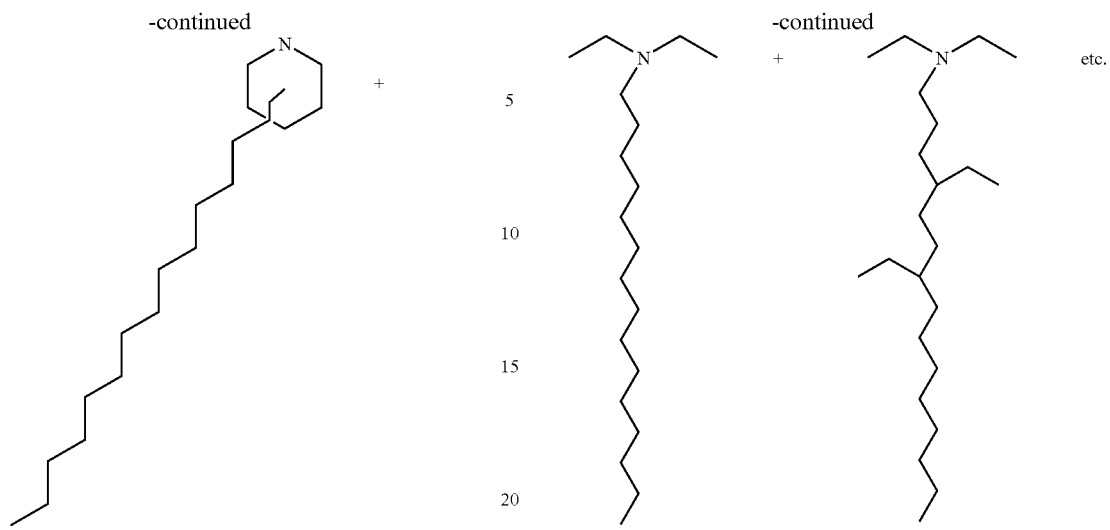

EXAMPLES 12–25

Metal Modified Copper Chromite Catalyst

In Example 12 an unpromoted copper chromite catalyst was modified by cobalt oxide addition in amounts of 1%, 2%, 5% and 10%, respectively. These catalysts were prepared by adding a certain amount of cobalt nitrate to the unpromoted catalyst, and that product was then dried at 100° C. before being calcined at 350° C. under nitrogen for eight hours. The modified catalysts were evaluated through a high throughput testing system using octylamine and methanol as starting materials. The individual vessel of this system had an internal volume of 30 mL. The cobalt-promoted copper chromite catalysts were charged to the reactor, and they were tested under the following conditions: octylamine:methanol=1:5; T=325° C.; and time=six hours. The reactors were purged with nitrogen before the temperature was increased. The product obtained after retrieval from the reactor was centrifuged to separate the catalyst. Based on GC, five multi-branched alkyl amine product clusters were obtained, and they were identified as monoalkyl, dialkyl, trialkyl, tetraalkyl and multialkyl groups. Products branched due to the presence of methyl and octyl groups were also identified.

With the use of a similar preparation method, a large number of catalysts with different promoters were prepared by modifying a $CuCr_2O_4$ catalyst with different metal ions. This included transition metal modification: $CuCr_2O_4$ promoted with 1%, 2%, 5%, and 10% Zn, Mn, Fe, Ni, and Mo (Examples 13–17), and base metal modification: $CuCr_2O_4$ promoted with 1%, 2%, 5%, and 10% K, Ba (Examples 18–19). Together with Ni molybdate/tungstate (Example 20) and Co molybdate (Example 21), these catalysts were evaluated under the same operating conditions as the cobalt-modified catalysts as described in Example 12.

A copper chromite catalyst promoted with 0.5%, 1%, and 2% Rh (Example 22), with 0.5%, 1%, and 2% Ag (Example 23), and with 0.5% and 1% Ru (Example 24) were also prepared followed the same procedure. Together with an unpromoted copper chromite catalyst (Example 25), they were evaluated under 280° C., instead of 325° C., for six hours to investigate noble metal modification for improved activity at lower temperature. Except for the differing reaction temperature, all of the other operating conditions were followed as described in Example 12.

Catalyst performance was evaluated based on activity and selectivity to branched products, selectivity to hydrocarbon byproducts and unbranded byproducts, and the effect of metal modification on the distribution of branched monoalkyl, dialkyl, trialkyl and multialkyl products. Product identification and quantitative analysis were conducted with GC/MS analysis. Table 1 summarizes the performance of the different metal-modified catalysts. It shows that the amount of metal loadings affected the product distribution. Cobalt-promoted copper chromite, Ni-molybdate/tungstate and cobalt-molybdate yielded higher branched monoalkyl products and lower branched heavier amine products. With a 325° C. reaction temperature and six hours testing time, the octylamine conversion was over 90% for all base-promoted and transition metal-promoted catalysts.

Rh and Ru-modified catalysts showed a higher rate of primary alkylamine conversion than the unpromoted copper chromite catalyst. Rh was particularly most active. It gave the highest conversion (over 80%) among the tested noble metals at a lower reaction temperature (280° C.). The 2% Rh provided a comparable selectivity of total branched products as other metals at 325° C.

TABLE 1

Summary of Metal-Modified Catalyst Performance

| Example | Catalyst | Conversion (%) | Selectivity TB/TP | Selectivity MonB/TB | Selectivity DB/TB | Selectivity MulB + TriB/TB |
|---|---|---|---|---|---|---|
| Example 12 | 1% Co | 99 | 46 | 46 | 27 | 27 |
| | 2% Co | 98 | 48 | 59 | 26 | 15 |
| | 5% Co | 97 | 39 | 35 | 31 | 34 |
| | 10% Co | 95 | 39 | 47 | 31 | 23 |
| Example 13 | 1% Zn | 97 | 55 | 18 | 35 | 48 |
| | 2% Zn | 95 | 58 | 11 | 28 | 61 |
| | 5% Zn | 100 | 59 | 29 | 49 | 22 |
| | 10% Zn | 95 | 58 | 22 | 47 | 32 |
| Example 14 | 1% Mn | 94 | 60 | 8.0 | 23 | 70 |
| | 2% Mn | 99 | 55 | 17 | 30 | 53 |
| | 5% Mn | 98 | 56 | 25 | 45 | 31 |
| | 10% Mn | 97 | 62 | 6.0 | 20 | 74 |
| Example 15 | 1% Fe | 99 | 63 | 9.0 | 25 | 67 |
| | 2% Fe | 98 | 59 | 6.0 | 23 | 71 |
| | 5% Fe | 99 | 50 | 33 | 31 | 36 |
| | 10% Fe | 95 | 59 | 10 | 29 | 61 |
| Example 16 | 1% Ni | 97 | 60 | 9.0 | 31 | 60 |
| | 2% Ni | 99 | 63 | 9.0 | 26 | 66 |
| | 5% Ni | 93 | 43 | 23 | 33 | 44 |
| | 10% Ni | 96 | 63 | 7.0 | 22 | 71 |
| Example 17 | 1% Mo | 98 | 63 | 9.0 | 26 | 65 |
| | 2% Mo | 99 | 66 | 12 | 30 | 58 |
| | 5% Mo | 97 | 60 | 13 | 25 | 62 |
| | 10% Mo | 98 | 63 | 9.0 | 25 | 66 |
| Example 18 | 1% K | 96 | 59 | 8.0 | 32 | 60 |
| | 2% K | 95 | 54 | 7.0 | 27 | 66 |
| | 5% K | 97 | 49 | 56 | 30 | 14 |
| | 10% K | 96 | 57 | 10 | 38 | 52 |
| Example 19 | 1% Ba | 98 | 67 | 3.0 | 33 | 64 |
| | 2% Ba | 100 | 64 | 12 | 29 | 60 |
| | 10% Ba | 99 | 53 | 36 | 42 | 23 |
| Example 20 | Ni molybdate/ tungstate | 92 | 54 | 53 | 25 | 22 |
| Example 21 | Co molybdate | 98 | 61 | 61 | 25 | 14 |
| Example 22 | 0.5% Rh | 94 | 12 | 19 | 42 | 39 |
| | 1% Rh | 89 | 24 | 10 | 28 | 62 |
| | 2% Rh | 82 | 47 | 3.0 | 23 | 74 |
| Example 23 | 0.5% Ag | 42 | 37 | 5.0 | 32 | 64 |
| | 1% Ag | 30 | 33 | 15 | 47 | 39 |
| | 2% Ag | 42 | 51 | 0.0 | 45 | 55 |
| Example 24 | 0.5% Ru | 68 | 25 | 14 | 42 | 45 |
| | 1% Ru | 68 | 27 | 14 | 48 | 38 |
| Example 25 | G13 (280° C.) | 58 | 35 | 15 | 35 | 50 |

TB: total branched products
TP: total products
MonB: Branched monoalkyl products
DB: Branched dialkyl products
TriB: Branched trialkyl products
MulB: Branched multialkyl products

EXAMPLE 26

Copper Chromite Catalyst with Differing Specifications

Copper chromite catalysts with different Cu/Cr ratios and surface areas were evaluated following the procedure described in Example 12 using the high-throughput testing system. With various Cu/Cr ratios and different surface areas, no significant difference was found in terms of the selectivity to total branched products. The tested copper chromite catalyst had a Cu % range of from 66 wt % to 40 wt %, a surface area range from 16 $m^2$/g to 50 $m^2$/g and a particle size range from 5 μm to 65 μm. Table 2 summarizes the performance of different copper chromite catalysts.

TABLE 2

Summary of Different Copper Chromite Catalyst Performance

| Cu wt % | Cr wt % | SA (m²/g) | PS (μm) | Conversion (%) | Selectivity TB/TP | Selectivity MonB/TB | Selectivity DB/TB | Selectivity MulB + TriB/TB |
|---|---|---|---|---|---|---|---|---|
| 40 | 26 | — | <65 | 95 | 42 | 14 | 29 | 57 |
| 40 | 26 | 50 | ~5 | 98 | 57 | 26 | 46 | 28 |
| 61 | 14 | 25 | 5 | 100 | 43 | 20 | 60 | 20 |
| 66 | 11 | 16 | 10 | 99 | 58 | 16 | 49 | 36 |
| 41 | 31 | 30 | 20 | 98 | 56 | 29 | 47 | 23 |
| 42 | 31 | 35 | 11 | 100 | 50 | 36 | 48 | 16 |
| 41 | 31 | 40 | 20 | 97 | 55 | 37 | 46 | 17 |
| 43 | 33 | 25 | <65 | 100 | 64 | 30 | 33 | 37 |

SA: surface area
PS: particle size

We claim:

1. A process for forming a branched molecular composition which comprises reading a reagent containing a saturated hydrocarbon moiety in the presence of (a) a catalyst capable of activating a carbon-hydrogen bond therein, wherein the catalyst is selected from the group consisting of copper chromite, copper molybdate, copper chromate, copper tungstate, copper vanadate and mixtures thereof, and (b) a branching reagent having a moiety that binds to the carbon atom in the carbon-hydrogen bond upon extraction of the hydrogen atom from that carbon-hydrogen bond.

2. The process as claimed in claim 1 wherein the catalyst is embedded in an anionic transition metal oxide or sulfide possessing a higher oxidation state for the metal therein than the metal in the cation.

3. A process as claimed in claim 2 wherein the transition metal in the anion is selected from the group consisting of the first, second, and third rows of Group lllB to VlB of the Periodic Table.

4. A process as claimed in claim 1 wherein the catalyst is modified with a modifier selected from the group consisting of the alkali metals, the alkaline earth metals, the post transition metal elements from Groups IIA to VIA of the Periodic Table of the Elements.

5. The process as claimed in claim 4 wherein the catalyst is copper chromite and said copper chromite is modified by the additional presence of rhodium.

6. The process of claim 1 wherein either, or both, of the substrate and the branching reagent contains a heteroatom, wherein said heteroatom is selected from the group consisting of nitrogen, sulfur, phosphorus, boron, oxygen, halogen, and mixtures thereof.

7. The process of claim 1 wherein the branching reagent is an amine or thiol group and the branching predominantly occurs at the beta position to said amine or thiol group.

8. The process of claim 1 wherein the branching reagent is a nitrile or thiophile and the branching predominantly occurs at the alpha position to the nitrile or thiophene group.

9. The process of claim 1 wherein the branching reagent is an aromatic compound and the branching takes the form of alkylation on the ring.

* * * * *

UNITED STATES PATENT AND TRADEMARK OFFICE
CERTIFICATE OF CORRECTION

PATENT NO. : 7,227,040 B2  Page 1 of 1
APPLICATION NO. : 10/862758
DATED : June 5, 2007
INVENTOR(S) : Zongchao Zhang and Xiaolei Sun It is certified that error appears in the above-identified patent and that said Letters Patent is hereby corrected as shown below:

Col. 13, line 20, change "reading" to --reacting--

Signed and Sealed this

Seventh Day of August, 2007

JON W. DUDAS
*Director of the United States Patent and Trademark Office*